(12) United States Patent
Doyle

(10) Patent No.: US 9,675,418 B2
(45) Date of Patent: Jun. 13, 2017

(54) POWERED SIGNAL CONTROLLED HAND ACTUATED ARTICULATING DEVICE AND METHOD OF USE

(75) Inventor: Mark Doyle, Del Mar, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 1347 days.

(21) Appl. No.: 13/521,165

(22) PCT Filed: Jan. 26, 2011

(86) PCT No.: PCT/US2011/022518
§ 371 (c)(1),
(2), (4) Date: Feb. 13, 2013

(87) PCT Pub. No.: WO2011/094269
PCT Pub. Date: Aug. 4, 2011

(65) Prior Publication Data
US 2013/0138118 A1   May 30, 2013

Related U.S. Application Data

(60) Provisional application No. 61/298,317, filed on Jan. 26, 2010.

(51) Int. Cl.
*A61B 19/00* (2006.01)
*F15B 7/00* (2006.01)
(Continued)

(52) U.S. Cl.
CPC .......... *A61B 19/2203* (2013.01); *A61B 34/30* (2016.02); *A61B 34/37* (2016.02);
(Continued)

(58) Field of Classification Search
None
See application file for complete search history.

(56) References Cited

U.S. PATENT DOCUMENTS

| 5,833,656 A | 11/1998 | Smith et al. |
| 5,841,950 A | 11/1998 | Wang et al. |

(Continued)

FOREIGN PATENT DOCUMENTS

| WO | WO 00/60521 A1 | 10/2000 |
| WO | WO 02/07608 A2 | 1/2002 |
| WO | WO2011/025818 | * 3/2011 |

OTHER PUBLICATIONS

European Search Report, dated Feb. 7, 2014, issued in European Patent Application No. 11737552.7.

Primary Examiner — Brian T Gedeon
(74) Attorney, Agent, or Firm — Arent Fox LLP

(57) ABSTRACT

An articulating device for aiding a user, such as, a surgeon or other medical practitioner, in manipulating a hand-actuated articulating device by providing a powered force used for moving the device, thus reducing or eliminating the need for the user to provide all the force required to move the device. The articulating device includes an input device, which receives one or more user inputs to direct a slave portion to perform work. The articulating device further includes a control portion that assists in transferring user input to the slave portion, and that further provides power assistance to at least partially drive the slave portion, in combination with the user input received by the input device.

33 Claims, 9 Drawing Sheets

(51) Int. Cl.
*A61B 34/30* (2016.01)
*A61B 34/37* (2016.01)
*A61B 17/00* (2006.01)
*A61B 90/00* (2016.01)

(52) U.S. Cl.
CPC ...... *F15B 7/00* (2013.01); *A61B 2017/00539* (2013.01); *A61B 2090/064* (2016.02)

(56) References Cited

U.S. PATENT DOCUMENTS

| | | |
|---|---|---|
| 5,943,914 A | 8/1999 | Morimoto et al. |
| 6,793,653 B2 | 9/2004 | Sanchez et al. |
| 7,470,268 B2 | 12/2008 | Doyle et al. |
| 2003/0144649 A1 | 7/2003 | Ghodoussi et al. |
| 2005/0200324 A1 | 9/2005 | Guthart et al. |
| 2009/0024120 A1 | 1/2009 | Sartor |

* cited by examiner

PID Controller
Others are:
Linear Quadratic Regulator (LQR)
Non-Linear/Adaptive

Another Example of PID

POWERED SIGNAL CONTROLLED HAND ACTUATED ARTICULATING DEVICE AND METHOD OF USE

This application is a National Phase entry of International Patent Application No. PCT/US11/22518, filed Jan. 26, 2011, which claims priority to U.S. Provisional Application No. 61/298,317, which was filed on Jan. 26, 2010, the entirety of which is hereby incorporated by reference herein.

BACKGROUND

Field of the Invention

Aspects of the present invention relate to signal controlled hand actuated articulating devices and methods of use thereof. One aspect of the present invention relates to a signal controlled hand-actuated articulating surgical instrument for use in minimally invasive surgical procedures, wherein the instrument includes a powered system therein.

Background of the Related Art

Laparoscopic surgery is known in the related art. However, current laparoscopic surgical instruments typically have straight bodies that are rather difficult to use. While such existing laparoscopic surgical instruments can perform invasive surgical procedures, the instruments are often awkward to manipulate around corners and other difficult to reach places. Moreover, related art articulating laparoscopic surgical instruments typically use cables and hydraulic lines to manipulate the surgical tip of the instruments. As the size of existing laparoscopic surgical instruments is reduced, the hydraulic lines used therein also typically decrease in size. However, when the hydraulic lines decrease in size, manually forcing hydraulic fluid through the hydraulic lines becomes more difficult to accomplish. Moreover, if a surgeon is controlling the surgical instrument within the body from a distance or at a remote location from the patient, the hydraulic lines may be relatively long, and thus manually forcing liquid through the hydraulic lines may become difficult to accomplish.

Thus, during prolonged surgical procedures, and/or in cases where the surgeon is at a remote location relative to the instrument and patient, the surgeon may experience hand fatigue.

SUMMARY

While discussion of the aspects of the present invention that follow describes surgery in an illustrative implementation, it should be appreciated that the environment according to variations of the present invention is not limited to surgery, and aspects hereof may be used in a variety of other implementations. For example, aspects of the present invention may be used in manufacturing, construction, assembly lines, handling and disposing of hazardous materials, underwater manipulations, handling high temperature materials, or any other suitable environment where a user may be remote from the item being manipulated or may experience fatigue when operating a mechanical device.

Aspects of the present invention aid a user, such as a surgeon or other such medical practitioner, in manipulating a hand-actuated articulating device by providing a powered force used for moving the device, thus reducing or eliminating the need for the user to provide all of the force required to move the device. Additional aspects of the present invention allow for the use of narrow diameter hydraulic tubes and other features.

BRIEF DESCRIPTION OF THE DRAWINGS

The disclosed aspects will hereinafter be described in conjunction with the appended drawings, provided to illustrate and not to limit the disclosed aspects, wherein like designations denote like elements, where.

DETAILED DESCRIPTION

Aspects of the present invention will now be described more fully herein with reference to the accompanying drawings, in which illustrate variations thereof will be shown. Aspects of the present invention may, however; be realized in many different forms and should not be construed as limited to the variations set forth herein; rather, the variations are provided so that this disclosure will be thorough and complete in illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

Figure 1:
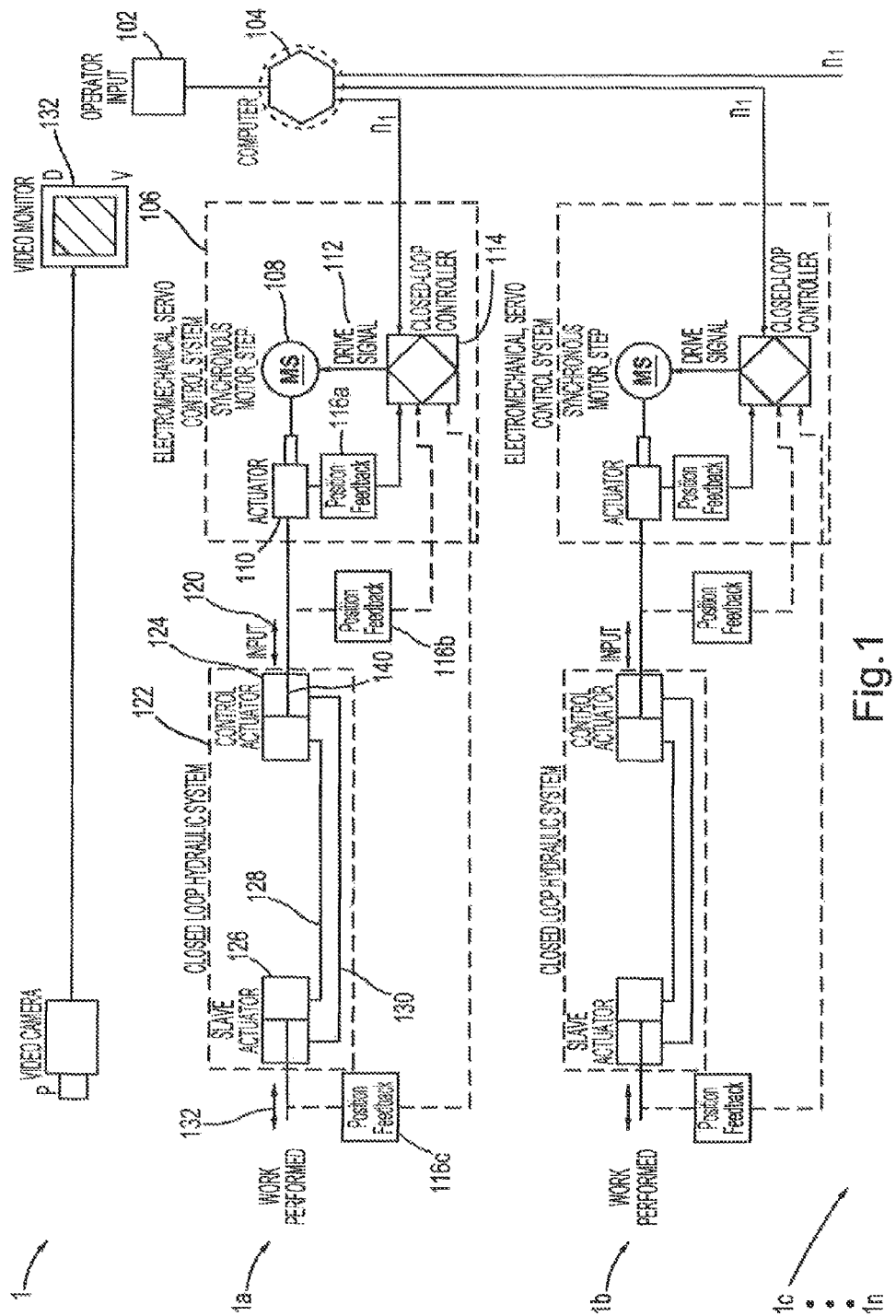
FIG. 1 is a schematic diagram of a signal control hand-actuated articulating device in accordance with an aspect of the present invention.

Turning now to FIG. 1, illustrated is a representative diagram of a signal controlled hand-actuated articulating system 1, in accordance with aspects of the present invention. The system 1 includes an input device 102, which receives one or more user master inputs to direct a slave portion 122 to perform work. System 1 further includes, a control portion 106 that assists in transferring user master input to the slave portion 122, and that further provides power assistance to at least partially drive the slave portion 122, in combination with the user master input received by the input device 102. System 1 may also include a video monitor 134 operationally connected to a video camera 136 for providing images of the work being performed by the functioning ends 132.

Figure 7:
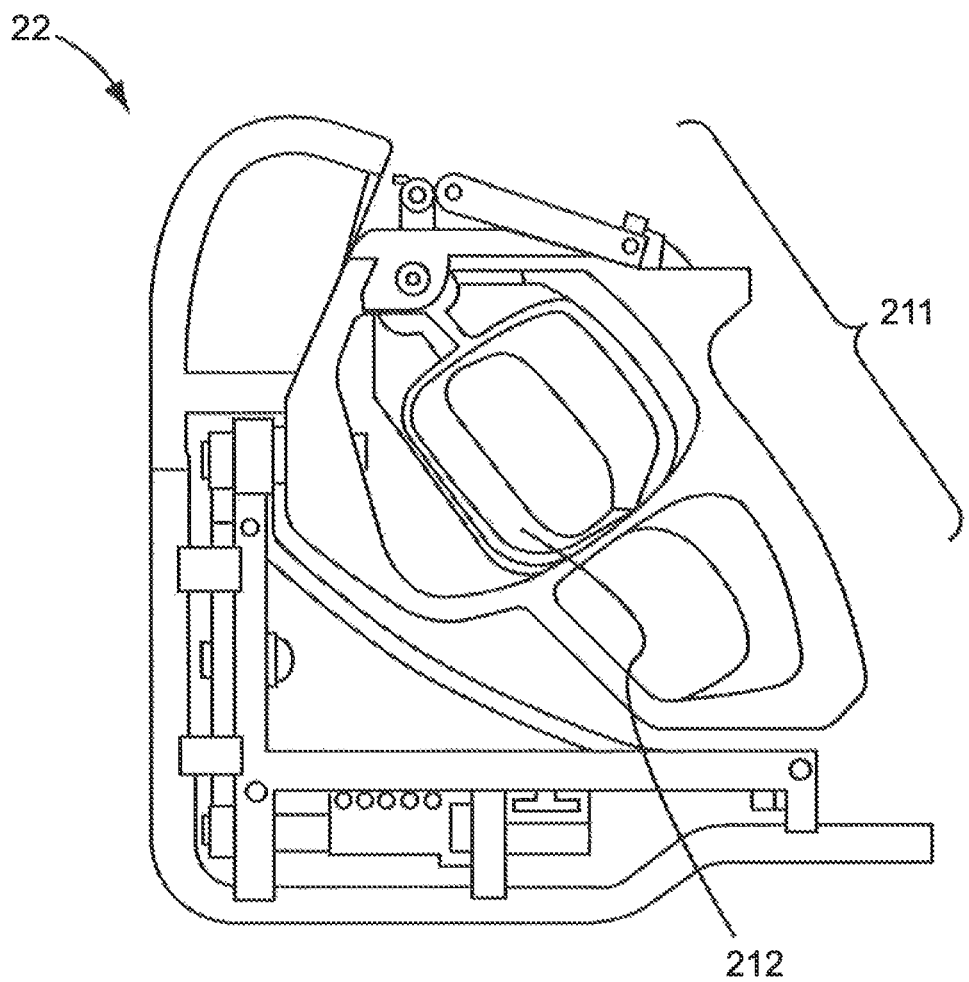
FIG. 7 is a perspective view of an aspect of a manipulator used in accordance with aspects of the present invention.
Figure 8:
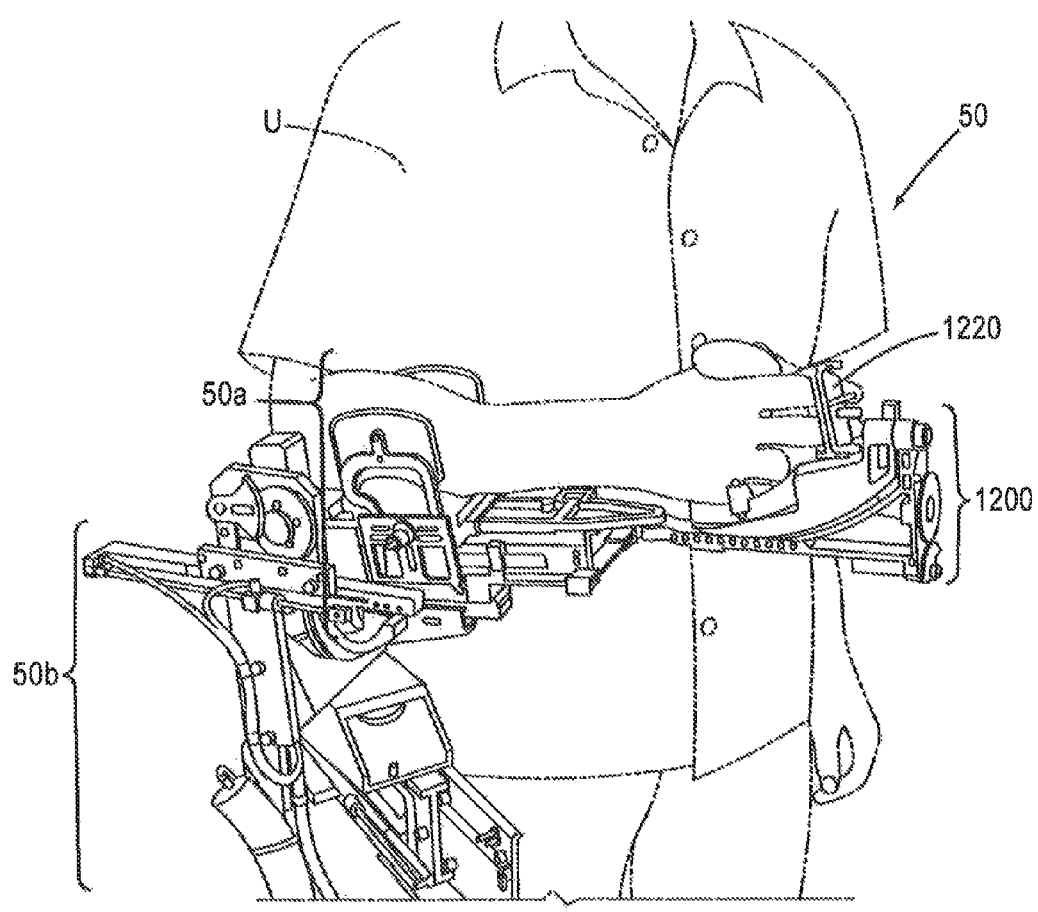
FIG. 8 is a perspective view of an aspect of a manipulator used in accordance with aspects of the present invention.

Input device 102 may include any suitable device or mechanism configured to receive one or more user master inputs, and to transmit all or some portion of the user master inputs, or a representation thereof, to an operating assist portion and/or the slave portion 122. The operating assist portion may include a control portion 106. For example, in an aspect, the input device 102 may have one or more input mechanisms to receive hand- or finger-actuated master inputs from a user of system 1. In other aspects, input device 102 may include input mechanisms to receive other inputs, such as foot-actuated inputs, arm- or body-actuated inputs, etc. from the user. In further aspects, input device 102 may include input mechanisms to receive voice- or audio-actuated or eye-actuated inputs from the user. Further, input device 102 may include one or more mechanisms and/or other features to transfer the one or more received master inputs to a master output, such as a connection portion interacting with the control portion 106 and/or the slave portion 122. As such, input device 102 may be operationally connected to the control portion 106. Input device 102 may include, for example, a joystick, a track ball, a rotary knob, an encoder, or a manipulator, among other input devices. Examples of input device 102 are illustrated in FIGS. 7 and 8.

It should be appreciated that the operating assist portion may be directly or indirectly connected to the input device 102 via the control portion 106. Control portion 106 may include any suitable system operable to receive a user master input, or a representation thereof, such as an electrical signal, and generate a master output to partially provide control, or other function, such as in combination with the user input or representation thereof, or fully control one or more functions of the slave portion 122. In an aspect, the control portion 106 includes a motor 108 that is operationally connected between a controller 114 and an actuator 110. Controller 114 receives all or a part of the user master input, or representation thereof, from the input device 102, and in response, generates a drive signal 112 that is received by the motor 108. Optionally, the controller 114 may additionally receive one or more feedback signals that also may affect the generation of the drive signal 112, as will be discussed in more detail below. Responsive to the drive signal 112, the motor 108 drives the actuator 110 to generate a master output 120, which is received by the slave portion 122 as a slave input to control, in whole or in part, the corresponding functioning end 132, which is coupled to the second slave end of the slave portion 122.

For example, the master output 120 may include a force, an electrical signal, a movement, or any suitable master input for driving the slave portion 122. Additionally, master output 120 may represent one or more of the user inputs received by the input device 102. In some aspects, for example, output 120 may be produced as a function of the received user input, wherein the function may be adjusted in any suitable manner in order to adjust an amount of force or effort required by a user in generating the one or more user inputs, in order to create a corresponding reaction/slave output by the slave portion 122 and/or the functioning end 132.

It should be appreciated that the motor 108 may include any suitable device that generates mechanical motion or force in response to electrical signals, such as electric signals that represent the user input received by input device 102 and forwarded to control portion 106. For example, the motor 108 may include solenoids, voice coil motors, stepper motors, and/or servo motors, among other devices suitable for generating mechanical motion and/or force in response to electrical signals.

In one variation, the input device 102 and the control portion 106 may be located outside of the patient's body, e.g., connected to and supported by the operating room table. In other aspects, one or more of the input device 102 and the control portion 106 may be located remote from the slave portion 122, e.g. in another room or location. Appropriate wired, wireless, and/or fiber optic couplings, for example, may be used to communicate between the input device 102 and the control portion 106 (also individually or collectively referred to herein interchangeably as "directly or indirectly coupled").

In addition, control portion 106 may be operationally connected to the slave portion 122. The slave portion 122 may include any suitable device or mechanism configured to receive one or more inputs, such as user inputs or representations thereof, from the control portion 106, and generate a corresponding output to control the functioning end 132 in a manner proportional to, or as a function of, the original user input. For example, in an aspect, slave portion 122 includes a double-acting closed loop hydraulic system including a control actuator 124 operationally connected to a slave actuator 126 having a first slave end and a second slave end communicating via hydraulic control lines 128, and 130. Additionally, a functioning end 132 is operationally connected to the second slave end or distal end of the slave actuator 126. In this exemplary implementation, the closed loop double-acting hydraulic circuit is the basic mechanical element used to transmit force to the distal end of the system 1, e.g. the slave portion 122. For example, the control actuator 124 receives an input, such as all or a portion of a user input or representation thereof, and transmits the input via one of the hydraulic control lines 128 or 130 to the first slave end of the slave actuator 126, which generates an output used to drive the functioning end 132 of the slave portion 122. In these aspects, the closed loop double-acting hydraulic system 1000 has similar functionality as disclosed in U.S. Pat. No. 6,607,475 which is incorporated herein in its entirety by reference. In another aspect, the slave portion 122 and the control portion 106 may be integrated into a single system.

The functioning end 132 receives, as an input, the slave output from the corresponding slave portion 112, and in response performs some work that is controlled as a function of one or more of the original user inputs received by the input device 102. As such, functioning end 132 may include any one or combination of devices or mechanisms configured to perform any suitable type of work. In an aspect of the present invention, the functioning end 132 may include a variety of tools. For example, the functioning end 132 may include one or any combination of a surgical tool, a surgical instrument, scissors, a knife, a screwdriver, a clamp, pliers, a suction/irrigation device, an electrosurgical device, or a visualization device, among other tools.

In operation, the user's hands, arms and/or fingers, for example, may guide the movement of system 1 by moving the input device 102. The inputted motion may be, for example, pushing, pulling, rotating, moving to the left, moving to the right, moving upwards, moving downwards, bending, spinning, grasping, tilting, moving diagonally, or any other suitable direction or combination of directions that may be necessary for system 1 to move. The input device 102 may include an actuator suitable for translating a user's movement into electrical signals. For example, input device 102 may include a sensor, an encoder, a control handle capable of rotating around an axis, and/or a manipulator, among other input devices capable of translating movement from a user into control signals. Examples of input device 102 are illustrated in FIGS. 7 and 8.

Turning now to FIG. 7, in one exemplary variation of an input device 102, in accordance with aspects of the present invention, the device 22 includes a handle 211, and a trigger loop 212 for interacting with the user. The user may grasp the handle 211, and place one or more fingers inside the trigger loop 212 and/or squeeze the trigger loop 212, as well as move the handle 211 in various directions. By squeezing the trigger loop 212, and/or by moving the handle 211, the user may cause an electrical signal to be generated, which in turn, is transmitted to the controller 114 (FIG. 1), resulting in a motion in the slave portion 122 (FIG. 1) (for example, an extend motion, a rotate motion, a bend motion, or a tool actuation). The user can then "open" the squeezed trigger loop 212, or move the handle 211 in another direction (e.g., opposite direction), to create another motion (e.g., opposite motion) in the slave portion 122. The trigger loop 212 may have one or more actuators for translating the movement of the handle 211 into electrical signals. The actuators may include, for example, one or any suitable combination of sensors, accelerometers or encoders, among other actuators. The trigger loop 212 may be sized to allow comfortable insertion of one or more human fingers. It should also be appreciated that handle 211 may have one or more trigger loops 212.

Turning now to FIG. 8, in another exemplary variation of input device 102, in accordance with aspects of the present invention, the device 50 features a grasper hand assembly 1200 and a trigger 1220 for interacting with the user. The user may grasp the grasper hand assembly 1200 and squeeze the trigger 1220, for example. By squeezing the trigger 1220, and/or by moving the handle 1200, the user may cause an electrical signal to be produced, which in turn, may be transmitted to the controller 114 (FIG. 1) and result in a motion in the slave portion 122 (FIG. 1) (for example, an extend motion, a rotate motion, a bend motion, or a tool actuation). The user can then "open" the squeezed trigger 1220, or move the handle 1200 in an opposite direction, for example, to create the opposite motion in the slave portion 122. The trigger 1220 may include one or more actuators for translating the movement of the hand assembly 1200 into electrical signals. The actuators may include, for example, one or any suitable combination of sensors, accelerometers or encoders, among other actuators.

In some aspects, the input device may be removably fixed to the arm of the user, such as by way of an optional clamp or strap. For example, such removable fixation may enhance correlation between a user movement and a received user input, as well as provide improved user comfort and allow for improved system safety.

It will be appreciated that the input device may take many other suitable forms. For example, the input device may be clamped to the side of a surgical bed and provided with handles or other features that may be grasped and/or manipulated by the surgeon. In another variation, the input device may be clamped to an object other than the surgical bed, such as a table or a cart. In yet another variation, the input device may be clamped to the user's arms or hand. In still another variation, the input device is held by the user, without being clamped to anything.

Figure 5:
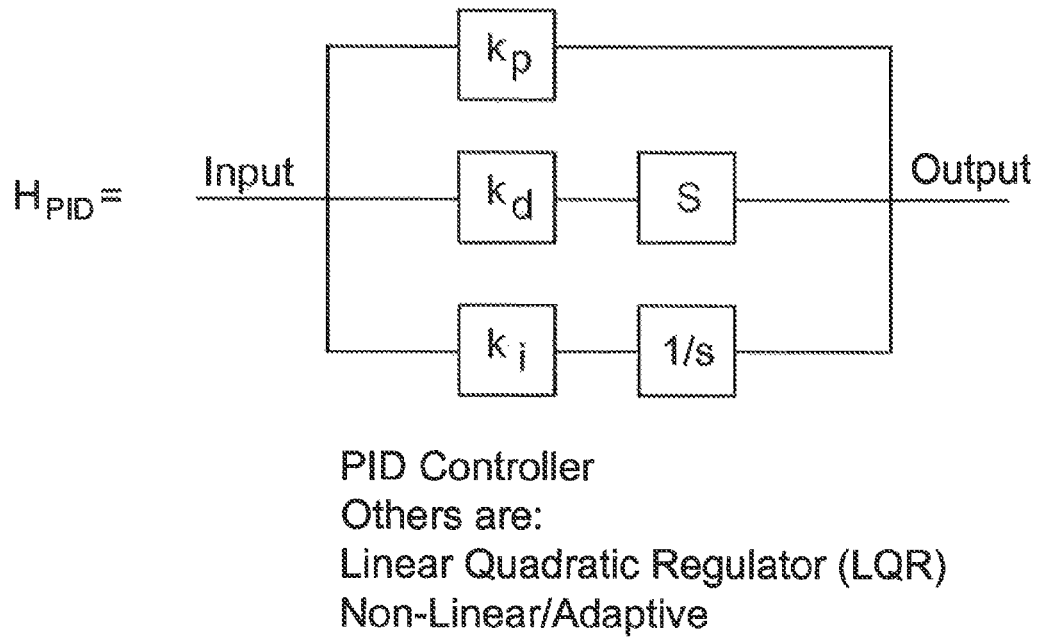
FIG. 5 is an example diagram of a proportional-integral-derivative (PID) algorithm used with an aspect of the present invention.
Figure 6:
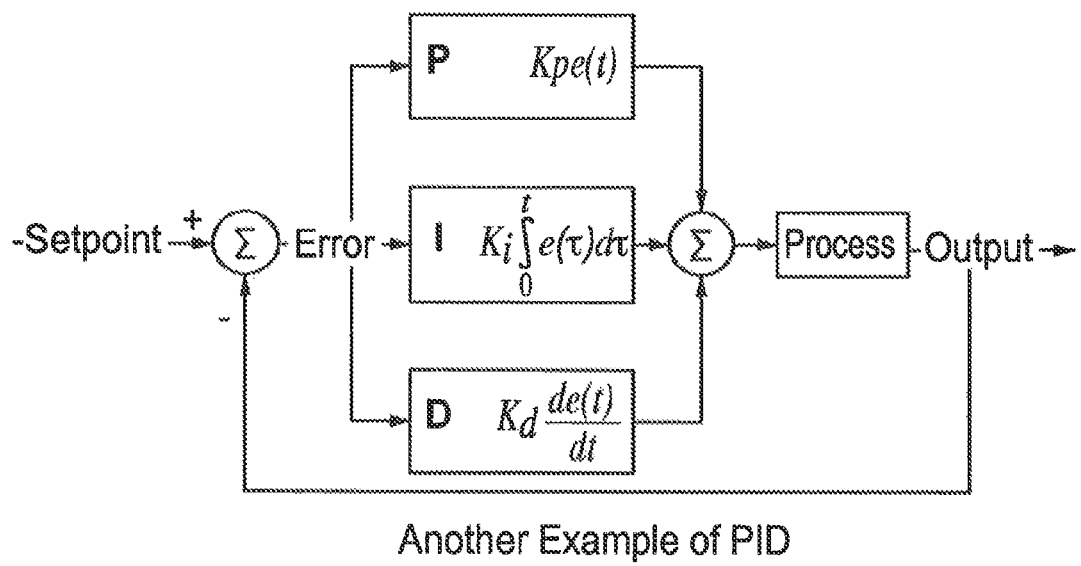
FIG. 6 is an example diagram of a PID algorithm used with another aspect of the present invention.

Referring again to FIG. 1, continuing with the operation of the system 1, the controller 114 receives a signal with the user's translated movement from the input device 102. The controller 114 processes the received signal from the input device 102 and, in turn, produces a drive signal 112 that is transmitted to the motor 108, providing an output motion corresponding to the inputted motion. In an aspect, the controller 114 may use a proportional-integral-derivative (PID) algorithm to control the actuation of the motor 108. For example, the controller 114 may use conventional RD algorithms, as illustrated in FIGS. 5 and 6, the output of the PID algorithms being a function of different components of the input.

Optionally, in one aspect, a processing device 104 may be operationally coupled between the input device 102 and the control portion 106. Processing device 104 may include, for example, a computer or other processing device, a position sensor, an encoder, a servo controller, or any other device capable of processing the motion inputted by the user. It should be appreciated that the processing device 104 may be directly or indirectly coupled to the input device 102 and/or the control portion 106.

Motor 108 transmits a force corresponding to the drive signal 112 received from the controller 114 to the actuator 110. Actuator 110 translates the received force from motor 108 into linear motion in a direction corresponding to the detected motion of the input device 102. The translation of the received input may be directly proportional to the generated output, or the relationship between the input and the output may be based on some other function or variable. For example, in an aspect, if the user moves the input device about 7 mm, then the motor may move the actuator about 7 mm. In other aspects, for example, the movement of the actuator may be greater than or less than the user movement. In any case, the resulting movement of the actuator 110 by the motor 108 may provide a force 120 to the control actuator 124 via the proximal end of the shaft 140, moving the shaft 140 in a direction corresponding to the direction of the movement of input device 102, for example.

Control actuator 124 may transmit the force 120 to the first slave end of the slave actuator 126 by moving fluid through hydraulic control lines 128, 130. It should be appreciated that the fluid may be any suitable hydraulic fluid, known or later developed, including, but not limited to water or saline. In a surgical environment, use of such fluids as saline may help avoid danger to a patient in the event of a leak, for example.

In an aspect, the slave actuator 126 is operationally connected to a distal end of control actuator 124, for example, via hydraulic lines, e.g. single acting or dual-acting. In an alternative aspect, the slave actuator 126 and control actuator 124 may be replaced with a mechanical element operationally connected to a distal, functional end 132 and a proximal end of the actuator 110, respectively. The mechanical element may include, for example, linkage gears, cams, one or a series of u-joints, push-pull wire or cable, a cable/pulley system, a cable gear shift system, a push-pull chain, a push-pull-rotate chain, lead screws, a push-pull flexible strap, a flexible steel band, or any suitable combination of these mechanical elements (e.g. a series of u-joints and a push-pull chain), among other mechanical elements. In an aspect, the movement of the functioning end 132 may be proportional to, or produced as a function of, the input provided to input device 102. For example, if the user moves the input device 4 mm, the controller may scale down the user input so that the functioning end moves 2 mm. It should be appreciated that the input may be scaled by the input device 102, the controller 114, and/or the slave portion 122, and may not be linearly transmitted.

The functioning end 132 may be operationally connected to the second slave end or distal end of slave actuator 126. The slave actuator 126 actuates the movement of the functioning end 132 in the direction of the force 120. Thus, the functioning end 132 moves corresponding to the direction of the motion. For example, if a surgeon pushes, pulls, rotates, grasps, tilts, moves to the left, moves to the right, moves upwards, moves downwards, bends wrist or fingers, or spins the input device 102, then the slave cylinder 126 may move the functioning end 132 in a similar manner, as some function of the user input, based upon the individual structure of the functioning end 132 and the connection thereto.

Figure 9:
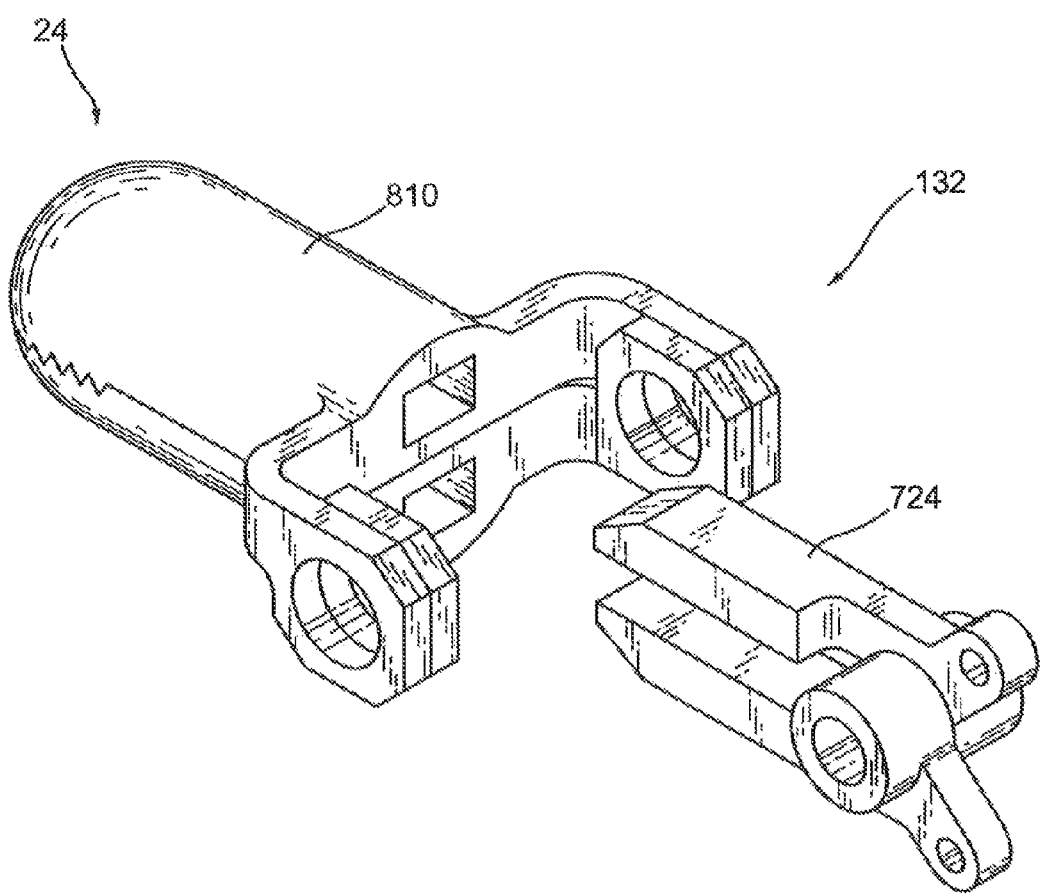
FIG. 9 is a perspective view of a remote functioning end used in accordance with aspects of the present invention.

Turning now to FIG. 9, illustrated is an example of a functioning end 132 operable for performing opening and closing operations, in accordance with aspects of the present invention. In one aspect, functioning end 132 may include an end effecter 810 and tines 724. Control tines 724 may be operable to move relative to one another and may be used for work. For example, the control tines 724 may be used for holding, gripping, or cutting, among other types of work. In an aspect, the tines 724 may be operationally connected to the slave actuator 126 (FIG. 1) and the end effecter 810. The tines 724 may rotate about a first axis, and the end effecter 810 may rotate about a second axis, with the first axis and second axis being substantially along the same line, e.g. concentric, when the end effecter 810 is connected to the tines 724. When moved, the tines 724 may in turn control the opening and closing motion of the end effecter 810. As noted, although the illustrated end effecter 810 is a clamping device, other tools may be mounted on the tines 724. For example, an end effecter 810 may include one or a combination of a surgical instrument, scissors, a knife, a screwdriver, clamps, pliers, a suction/irrigation device, an electrosurgical device, or a visualization device, among other tools that may be mounted on the tines 724.

Referring again to FIG. 1, in an aspect, a feedback device 116*a* is located within the control portion 106 and is operationally coupled between the actuator 110 and the controller 114. The feedback device 116*a* may track the movement of the actuator 110, for example, converting the position information of the actuator 110 into electrical signals, which are transmitted to the controller 114. It should be appreciated that feedback device 116*a* may include any suitable sensor capable of indicating a position, e.g., a digital encoder. The controller 114 may compare the received signal from the feedback device 116*a* with the received signal from the processing device 104, for example, preventing further movement of the actuator 110 once the movement of actuator 110 is the same as, or within some range of, the movement of the input device 102. For example, if the user moves the input device 7 mm, when the feedback device detects that the motor has moved the actuator 7 mm, the controller may prevent further movement of the actuator. Thus, the feedback device 116*a* may prevent the actuator 110 from moving past a limit and/or out of control, for example.

As noted above, the video monitor 134 may provide visual feedback to the user of the movement and the work being performed by the functioning ends 132. If the user visually recognizes that the functioning end 132 does not move the entire distance input, for example, the user may correct the position of the functioning end 132 by further moving the input device 102. Through experience, the user may be able to learn from the feedback device 116*a* at the actuator side what the result would be at the functioning end side. Thus, the user may be able to correct discrepancies in movement of the functioning end 132. In other aspects, the system 1 may include a system setup routine to calibrate the controller to translate a user master input into a given slave portion 122 or slave output at the functioning end 132, within a certain tolerance, which may be dictated by the components used in the system 1. It should be appreciated that the feedback device 116*a* may also be outside of the control portion 106, operationally coupled to the controller 114 between the actuator 110 and slave portion 122, for example, as illustrated by the feedback device 116*b*. In addition, it should be appreciated that the feedback device 116*a* may alternatively be operationally coupled to the controller 114 between the functioning end 132 and the controller 114, for example as illustrated by the feedback device 116*c*.

It should be appreciated that system 1 may have various sub-systems, for example, component sets 1*a*, 1*b*, and 1*c* of FIG. 1, for producing different motions. Sub-systems 1*a*, 1*b* and 1*c* may include any suitable combination of input devices 102, control portion 106, slave portion 122 and functioning ends 132, for example. In the illustrated example, a single input device 102 is coupled to at least two separate combinations of control portions 106, slave portions 122 and functioning ends 132, thereby enabling a user to generate at least two different functions at the two functioning ends 132. The individual systems may be activated as a result of receiving appropriate user input, e.g., pressing on an actuator located on the input device or moving the input device in the desired direction. For example, individual sub-systems may be provided for each of the following motions: pushing, pulling, rotating, moving to the left, moving to the right, moving upwards, moving downwards, bending, spinning, moving diagonally, among other motions. It should be appreciated that the number of systems included in system 1 for controlling the direction of movement by the functioning end may depend on the range of motion the user desires for the functioning end and the structure thereof.

Figure 2:
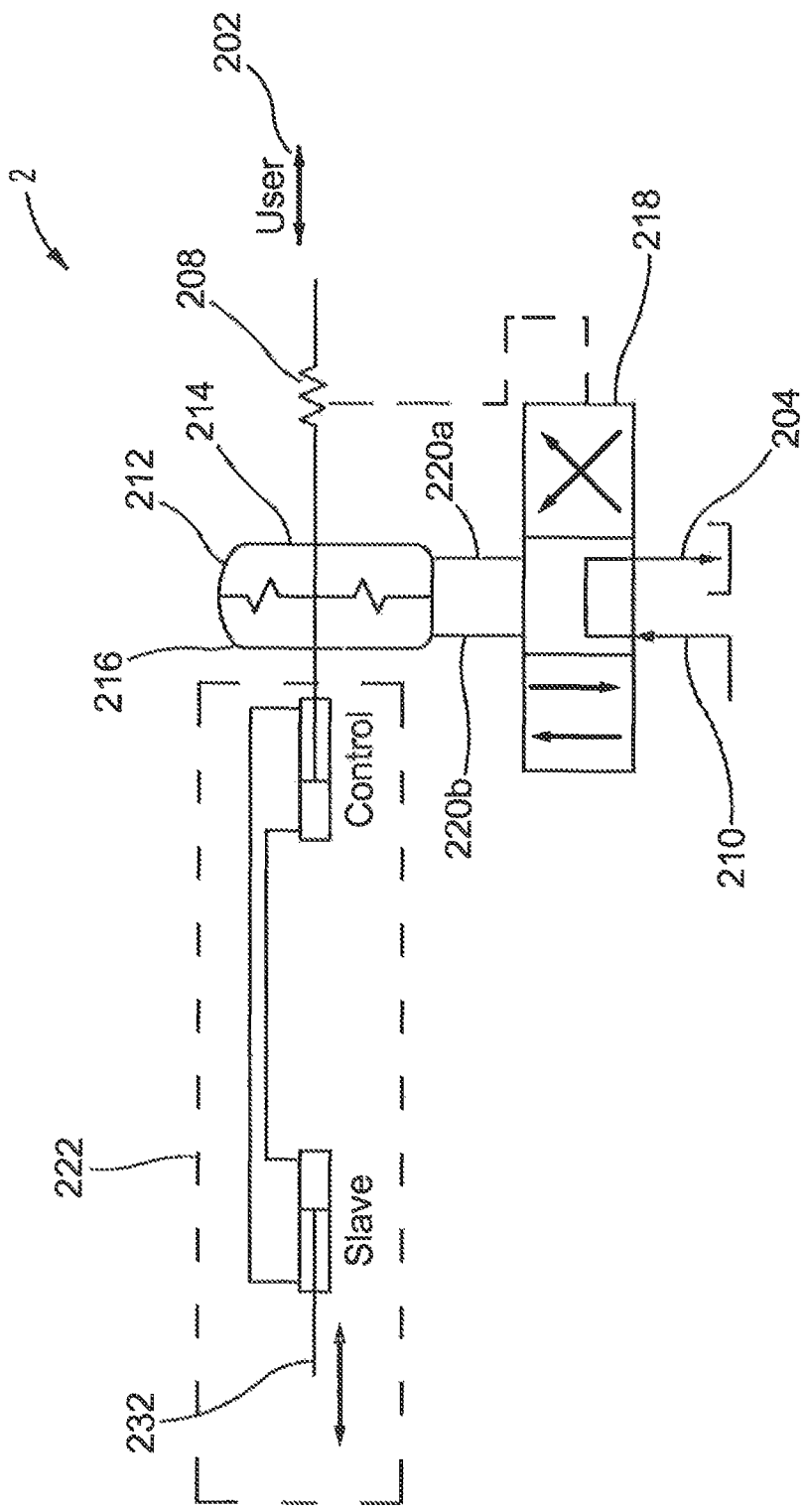
FIG. 2 is a schematic diagram of a pressure controlled hand-actuated articulating device in accordance with yet another aspect of the present invention.

Turning now to FIG. 2, illustrated is a representative diagram of an exemplary hand-actuated articulating device 2 for use with a pressure assist system, e.g., mechanical vacuum pressure, for translating received user input(s) into output(s) or work at one or more functioning ends 220. Additional force is applied when moving the functioning ends, which may compensate for friction or other resistance to motion, for example, thereby easing movement of the functioning ends. Moreover, since the user is mechanically operating to the system, the user may receive tactile feedback for the work being performed by the functioning ends.

In an aspect, device 2 includes an input device 202, a dual acting diaphragm 212 as the control portion, a valve 218 and a slave portion 222. Input device 202 may be operationally connected to the proximal side 214 of diaphragm 212. The valve 218 may be operationally connected to the proximal side 214 of the dual acting diaphragm 212 via line 220*a*, and to the distal side 216 of the dual acting diaphragm 212 via line 220*b*. The slave portion 222 is operationally connected to the distal side 216 of the dual acting diaphragm 212. It should be appreciated that the slave portion 222 may have similar functionality and components to the double-acting closed loop hydraulic system discussed in FIG. 1.

In an aspect, as the user moves input device 202 forward or backward, for example, left and right as shown in FIG. 2, the valve 218 actuates. Thus, as the user moves the input device 202 forward (e.g., left in FIG. 2), an operative connection moves the valve 218. The actuation of the valve 218 controls a pressurized fluid moving into the valve via line 210 and moving out of the valve via line 204. In one aspect, the valve 218 may electrically control the movement of the pressurized fluid through the valve proportional to the user's displacement, for example. The valve 218 thereby admits a pressure to the proximal side 214 of the dual acting diaphragm 212 via line 220a. The pressure from the valve 218 causes the dual acting diaphragm 212 to move, pushing a fluid through the slave portion 222, and thus "helping" the user (e.g., a surgeon) move the functioning end 232 forward. The valve 218 and diaphragm 212 thereby act as an amplifier of the user's motion. In addition, if the user pulls backs the input device 202 (e.g., moves right in FIG. 2), the valve 218 reverses the pull on the dual acting diaphragm 212 via line 220b, helping the functioning end 232 to move backward (e.g., to the right in FIG. 2). Thus, as the valve 218 actuates, the fluid may be pushed through the slave portion 222, proportional to the user's displacement, causing the functioning end 232 to move in a forward direction or backwards. Optionally, in one aspect, a control device may be operationally connected between the input device 202 and the valve 218. The control device may include, for example, a computer or other processing device, a position sensor, an encoder, a servo controller, and/or any other suitable device capable of processing the motion inputted by the user. It should be appreciated that the control device may be directly or indirectly connected to the input device 102 and/or the valve 418.

Figure 3:
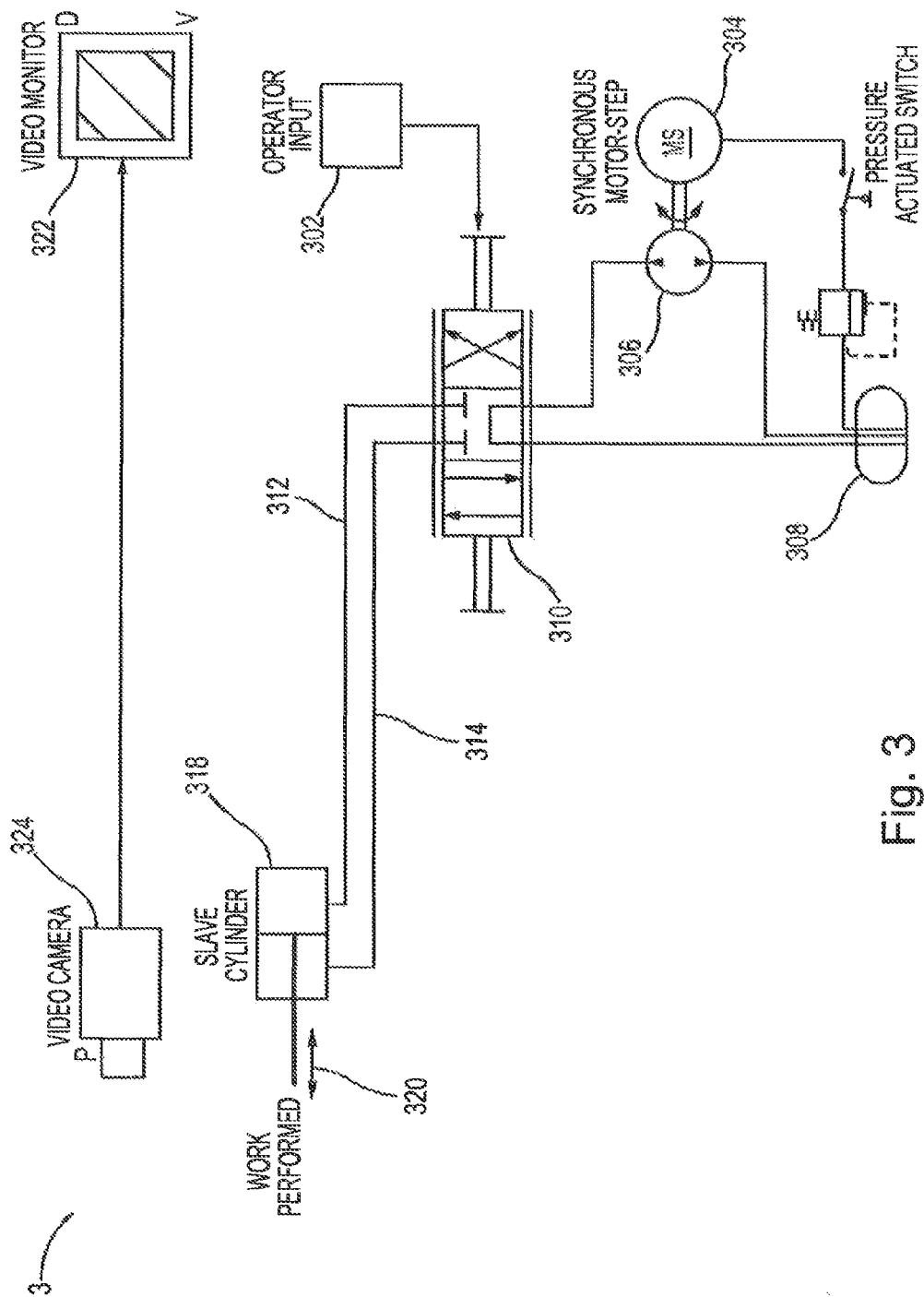
FIG. 3 is a schematic diagram of a mechanically controlled hand-actuated articulating device in accordance with yet another aspect of the present invention.

Turning now to FIG. 3, illustrated is a representative diagram of an exemplary device 3, having similar functionality as described above for device 2 of FIG. 2, but employing a mechanical system as the control portion to translate the received user input(s) into output(s) or work at one or more functioning ends 320.

In an aspect, device 3 includes an input device 302, a valve 310 as part of a control portion and a slave actuator 318. Input device 302 is operationally connected to the valve 310. The valve 310 is operationally connected to the slave actuator 318. Slave actuator 318 is operationally connected to one or more functioning ends 320. In an aspect, as the user moves input device 302 forward or backward, for example, valve 310 actuates. Thus, as the user moves the input device 302 forward, an operative connection moves the valve 310. The actuation of the valve 310 controls the flow of fluid from a fluid reservoir 308 to the slave actuator 318 via hydraulic control lines 312, 314. The movement of the slave actuator 318 in turn produces the work performed by functioning ends 320.

Device 3 may further include a pressure source, such as a pump system, or tank-stored gases, among other pressure sources, for powering the actuation of the valve 310 as part of the control system. The pump system may include a motor 304, for example, that is operationally connected to a pump 306 and a fluid reservoir 308. In an aspect, the motor 304 drives the pump 306, and in response, the pump 306 pumps fluid from the reservoir 308 to the valve 310. Since the motor powers the actuation of the valve, the user may not receive tactile feedback when moving the input device in this variation.

Figure 4:
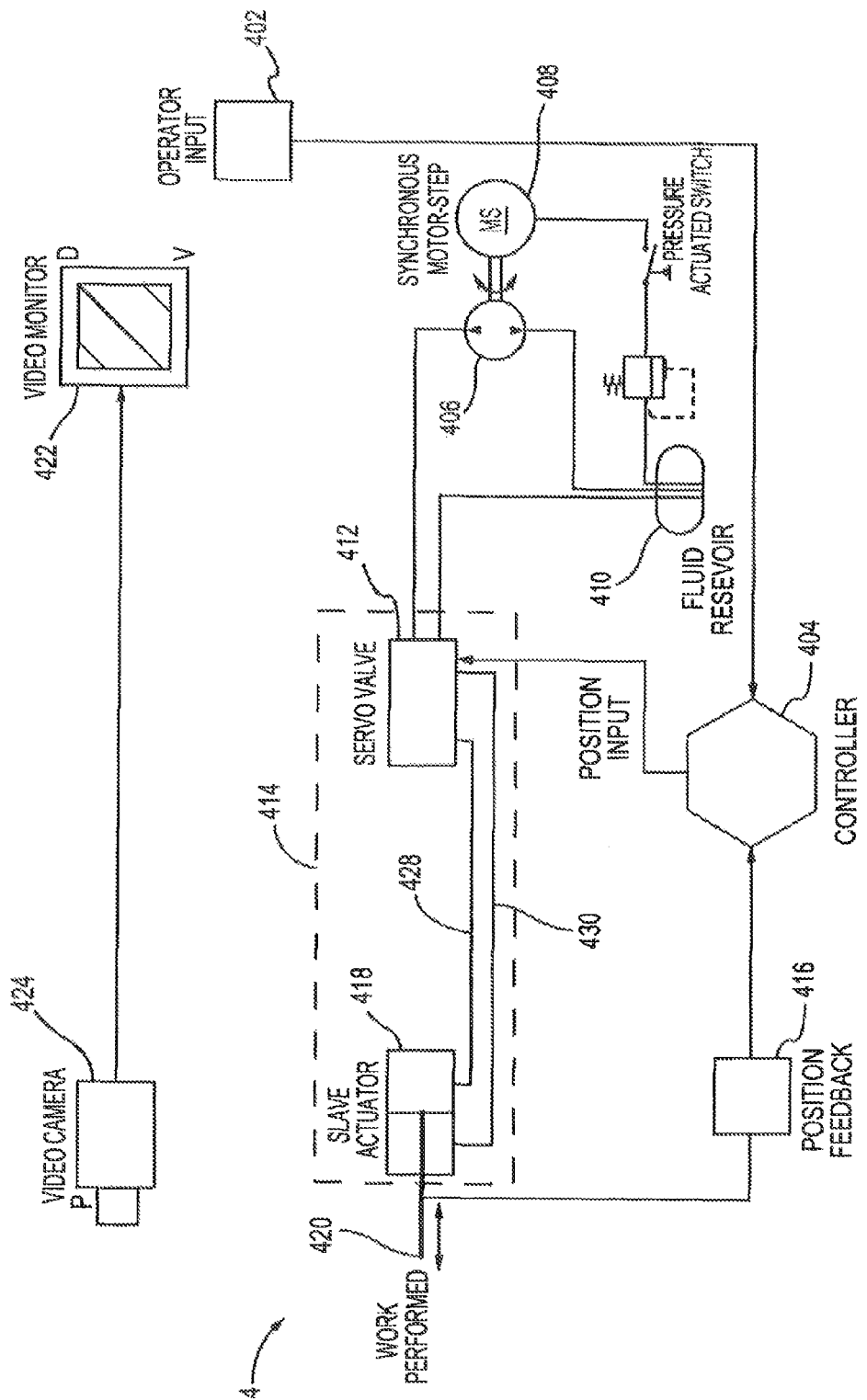
FIG. 4 is a schematic diagrams of hydraulic systems usable in accordance with aspects of the present invention.

Referring now to FIG. 4, illustrated is a representative diagram of device 4, having similar functionality as described above with system 1 of FIG. 1, but employing a hydraulic system as the control portion to translate the received user input(s) into output(s) or work at one or more functioning ends 420. Similar to as discussed above, device 4 includes an input device 402, a controller 404 as part of the control system and a slave portion 414. The controller 404 receives the user input(s) from the input device 402 and controls the movement of the slave portion 414, based upon the received user input(s). The slave portion 414 may include a slave actuator 418 that is operationally connected between one or more valves 412 and one or more functioning ends 420, for example.

In an aspect, the controller 404 is operationally coupled between the input device 402 and one or more of the valves 412. Controller 404 receives the user input(s) from the input device 402 and transmits a position input to the valve 412. The input device 402 may be similar to that described in the examples above, including, for example, an encoder, a control handle capable or rotating around an axis, and/or a manipulator, among other input devices. In response to the received position input from the controller 404, valve 412 regulates the flow of fluid from a fluid reservoir 410 to the slave actuator 418 via hydraulic control lines 428 and 430. It should be appreciated that the controller 404 may be directly or indirectly coupled to the input device 402 and the valve 412.

Device 4 may further include a pump portion for powering the movement of the valve 412 as part of the control portion. The pump portion may include a motor 408, for example, that is operationally connected to a pump 406 and a fluid reservoir 410, each of which may be part of the control portion. In an aspect, the motor 408 drives the pump 406, and, in response to operation of the pump 406, pumps fluid from the reservoir 410 to the valve 412. Since the motor powers the actuation of valve, the user may not receive tactile feedback when moving the input device in this variation.

It should be appreciated that reservoir 410 may include any suitable device capable of holding hydraulic fluid. In addition, the pump 406 may include any suitable pump, for example, a synchronous motor step driven pump. Pressure sensors may be provided on the reservoir and/or the outlet of the pump and used to control the pump to maintain a desired fluid pressure being supplied to the valve 412. Other aspects may include a pressure activated switch to control the pump and thereby regulate the system pressure. The reservoir 410 may also include suitable filters, flow restrictors, and overpressure release valves, for example, as desired. It should be appreciated that a single reservoir 410 may be used to provide pressurized hydraulic fluid to one or more valves 412, for example. Alternatively, a separate reservoir may be provided for each valve 412. Other aspects may include a static pressurized fluid vessel, for example, pressurized by a pressurizing gas. The valve 412 may operate by controlling which of the hydraulic control lines 428, 430 through which hydraulic fluid flows, also, with controlling the pressure and rate of fluid flow through the lines.

A feedback device 416 may be operationally positioned between the slave actuator 418 and the controller 404. The feedback device 416 may be located within the slave portion 414, for example and operated to detect the position of slave actuator 418, and to relay that information to the controller 404. The controller 404 in turn may receive the position information for the slave actuator 418 and verify that the slave actuator 418 has moved the proper distance corresponding to the user input. If the slave actuator 418 did not move the proper distance, then the controller 404 may transmit another position input to the valve 412. In another aspect, the user may use a video monitor 422 operationally connected to video camera 424 for providing visual feedback of the position information for the slave actuator 418. If the functioning ends 420 did not move the appropriate distance, for example, the user may provide an additional input(s) to input device 402 for correcting the movement of the functioning ends 420.

In any of the above-described aspects, any suitable hydraulic fluid may be used. The fluid may comprise sterilized distilled water; however a saline solution, a perfluorinated hydrocarbon liquid, or any other physiologically compatible fluid may also be used. A "physiologically compatible fluid" may include a fluid that, once exposed to tissues and organs, does not create any intolerable reaction, such as a rash or immune response in the patient, and thus does not adversely interfere with the normal physiological function of the tissues or organs to which it is exposed. In addition, a physiologically compatible fluid may ideally remain in a patient's body or in contact with a tissue or an organ without the need to remove the fluid for patient safety or health.

One variation of the present invention may include features for a surgeon or other user to control multiple sensing elements and/or electric or other controllable elements for creating different motions. For example, individual systems may be provided for pushing, pulling, rotating, moving to the left, moving to the right, moving upwards, moving downwards, bending, spinning, moving diagonally, among other operators. The individual systems may be activated, for example, in response to the appropriate hand motions by a surgeon.

Figure 10:
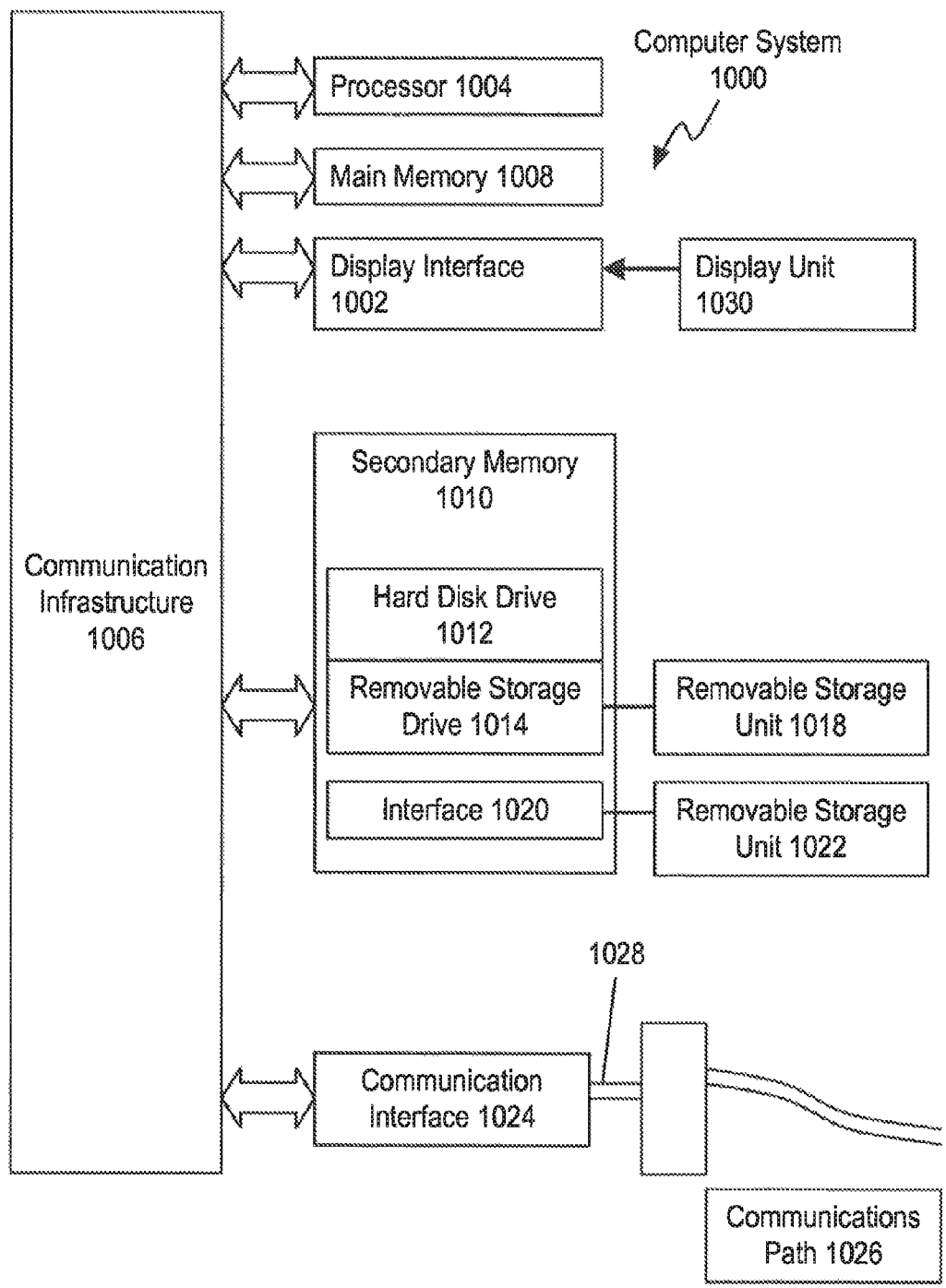
FIG. 10 presents an exemplary system diagram of various hardware components and other features, for use in accordance with aspects of the present invention.

Aspects of the present invention may be implemented using hardware, software, or a combination thereof and may be implemented in one or more computer systems or other processing systems. In one variation, aspects of the invention are directed toward one or more computer systems capable of carrying out the functionality described herein. An example of such a computer system 1000 is shown in FIG. 10.

Computer system 1000 includes one or more processors, such as processor 1004. The processor 1004 is connected to a communication infrastructure 1006 (e.g., a communications bus, cross-over bar, or network). Various software aspects are described herein in terms of this exemplary computer system. After reading this description, it will become apparent to a person skilled in the relevant art(s) how to implement aspects of the invention using other computer systems and/or architectures.

Computer system 1000 may include a display interface 1002 that forwards graphics, text, and other data from the communication infrastructure 1006 (or from a frame buffer not shown) for display on a display unit 1030. Computer system 1000 also may include a main memory 1008, preferably random access memory (RAM), and may also include a secondary memory 1010. The secondary memory 1010 may include, for example, a hard disk drive 1012 and/or a removable storage drive 1014, representing a floppy disk drive, a magnetic tape drive, an optical disk drive, etc. The removable storage drive 1014 reads from and/or writes to a removable storage unit 1018 in a well-known manner. Removable storage unit 1018 represents a floppy disk, magnetic tape, optical disk, etc., which is read by and written to removable storage drive 1014. As will be appreciated, the removable storage unit 1018 may include a computer usable storage medium having stored therein computer software and/or data.

In alternative variations, secondary memory 1010 may include other similar devices for allowing computer programs or other instructions to be loaded into computer system 1000. Such devices may include, for example, a removable storage unit 1022 and an interface 1020. Examples of such may include a program cartridge and cartridge interface (such as that found in video game devices), a removable memory chip (such as an erasable programmable read only memory (EPROM), or programmable read only memory (PROM)) and associated socket, and other removable storage units 1022 and interfaces 1020, which allow software and data to be transferred from the removable storage unit 1022 to computer system 1000.

Computer system 1000 may also include a communications interface 1024. Communications interface 1024 allows software and data to be transferred between computer system 1000 and external devices. Examples of communications interface 1024 may include a modem, a network interface (such as an Ethernet card), a communications port, a Personal Computer Memory Card International Association (PCMCIA) slot and card, etc. Software and data transferred via communications interface 1024 may be in the form of signals 1028, which may be electronic, electromagnetic, optical or other signals capable of being received by communications interface 1024. These signals 1028 are provided to communications interface 1024 via a communications path (e.g., channel) 1026. This path 1026 carries signals 1028 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1080, a hard disk installed in hard disk drive 1070, and signals 1028. These computer program products provide software to the computer system 1000. Aspects of the invention are directed to such computer program products.

Computer programs (also referred to as computer control logic) are stored in main memory 1008 and/or secondary memory 1010. Computer programs may also be received via communications interface 1024. Such computer programs, when executed, enable the computer system 1000 to perform various features in accordance with aspects of the present invention, as discussed herein. In particular, the computer programs, when executed, enable the processor 1010 to perform various functions in accordance with aspects of the present invention. Accordingly, such computer programs represent controllers of the computer system 1000.

In a variation where aspects of the invention are implemented using software, the software may be stored in a computer program product and loaded into computer system 1000 using removable storage drive 1014, hard delve 1012, or communications interface 1020. The control logic (software), when executed by the processor 1004, causes the processor 1004 to perform the functions of the invention as described herein. In another variation, aspects of the invention are implemented primarily in hardware using, for example, hardware components, such as application specific integrated circuits (ASICs). Implementation of the hardware state machine so as to perform the functions described herein will be apparent to persons skilled in the relevant art(s).

In yet another variation, aspects of the invention are implemented using a combination of both hardware and software.

Although aspects of the invention have been described with reference to various examples with respect to surgical instruments, it is within the scope and spirit hereof to incorporate or use such devices and systems with any suitable mechanical application. Further, while aspects of the invention have been described with reference to a surgeon, various features may be used with another user, depending on circumstances in which such devices and systems are used. Thus, it should be understood that numerous and various modifications may be made hereto without departing from the spirit hereof.

What is claimed is:

1. An articulating device, comprising:
   an input device capable of receiving an input and producing a master output;
   a slave actuator coupled to the input device operable to receive the master output from the input device and to generate a corresponding slave output, wherein the slave actuator comprises a first slave end and a second slave end, the first slave end being coupled to the input device;
   a functioning end coupled to the second slave end, wherein the functioning end performs the slave output; and
   an operating assist portion operable with the input device and to assist with translating the master output received by the slave actuator into the corresponding slave output performed by the functioning end,
   wherein the operating assist portion comprises a dual acting diaphragm and is further operable to provide power assistance to at least partially drive the slave actuator in combination with the input received by the input device.

2. The articulating device of claim 1, wherein the operating assist portion comprises: a valve operatively connected to the input device and the first slave end.

3. The articulating device of claim 2, wherein the dual acting diaphragm includes a proximal side and a distal side, wherein the proximal and distal sides of the dual acting diaphragm are coupled to the valve via at least one fluid line.

4. The articulating device of claim 3, wherein actuation of the valve admits a pressure on one of the proximal and distal sides of the dual acting diaphragm via one of the at least one fluid line.

5. The articulating device of claim 1, wherein the slave output performed by the functioning end is proportional to the master input.

6. The articulating device of claim 3, further comprising:
   a control device capable of processing the operation of the input device, wherein the control device is operationally connected to the input device and the valve.

7. The articulating device of claim 2, further comprising:
   a pressure source operationally connected to the valve and a fluid reservoir, wherein operation of the pressure source pressurizes a hydraulic fluid communicating the input device and the valve via hydraulic lines.

8. The articulating device of claim 7, wherein the input device and the valve communicate via hydraulic lines.

9. The articulating device of claim 7, wherein the pressure source includes a pump.

10. The articulating device of claim 2, further comprising:
    a controller capable of controlling the operation of the input device, wherein the controller is operationally coupled with the input device and the valve.

11. The articulating device of claim 10, wherein the valve regulates flow of hydraulic fluid to the first slave end via a hydraulic line.

12. The articulating device of claim 11, further comprising:
    a pressure sensor provided on at least one of the pressure source and the reservoir, wherein the pressure source operates to maintain a fluid pressure based on a pressure sensed by the pressure sensors.

13. The articulating device of claim 10, further comprising:
    a feedback device operationally coupled to the slave actuator and the controller, wherein the feedback device detects a position of the slave actuator.

14. The articulating device of claim 13, wherein the controller provides a position input to the valve actuator based on the position of the slave actuator as detected via the feedback device.

15. The articulated device of claim 1, further comprising:
    a video camera for providing visual feedback of a position of the valve actuator.

16. The articulated device of claim 1, wherein the input device comprises:
    a handle; and
    a trigger loop.

17. The articulated device of claim 16, wherein the trigger loop comprises:
    at least one translating actuator that translates a movement of the handle into an electrical signal.

18. The articulated device of claim 1, wherein the input device comprises: a grasper hand assembly and a trigger.

19. The articulated device of claim 18, wherein the trigger comprises:
    at least one translating actuator that translates a movement of the handle into an electrical signal.

20. The articulated device of claim 1, wherein the functioning end comprises:
    an end effecter; and
    a plurality of tines, wherein motion of the plurality of tines is produced by operation of the slave actuator and the end effecter.

21. The articulated device of claim 20, wherein the plurality of tines are rotatable about a first axis, and wherein the end effecter is rotatable about a second axis.

22. The articulated device of claim 1, further comprising:
    a motor;
    a controller;
    a control actuator; and
    a feedback device;
    wherein the motor and the feedback device are each operationally connected with the control actuator and the controller.

23. The articulated device of claim 22, wherein the controller receives an input signal from the input device and a feedback signal from the feedback device and generates a drive signal received by the motor, and wherein the motor drives the control actuator based on the received drive signal.

24. The articulated device of claim 23, wherein the control actuator generates a control output that is received by the slave actuator.

25. The articulated device of claim 24, wherein the control output that is received by the slave actuator controls the functioning end.

26. The articulated device of claim 24, wherein the controller is configured to use a proportional-integral-derivative (PID) algorithm to control actuation of the motor.

27. The articulated device of claim 22, wherein, the controller further comprises:
    a processing device operationally coupled to the input device;
    wherein the processing device generates a processor signal based on a movement of the input device.

28. The articulated device of claim 27, wherein the processing device is selected from a group consisting of a computer, a position sensor, an encoder, and a servo controller.

29. The articulated device of claim 22, wherein the slave actuator is connected to a distal end of the control actuator.

30. The articulated device of claim 27, wherein the feedback signal is generated based on a movement of the control actuator.

31. The articulated device of claim 30, wherein the controller compares the feedback signal with the processor signal and prevents movement of the control actuator when the feedback and processor signals indicate that the movement of the control actuator is beyond a predetermined range.

32. A method of operating an articulating device comprising:
- moving an input device;
- transmitting a master input from the input device to a slave actuator, the slave actuator comprising a first slave end and a second slave end, wherein the slave actuator is coupled to the input device;
- translating the master input into a master output via an operating assist portion; and
- transmitting the master output via the operating assist portion to a functioning end coupled to the second slave end, wherein the functioning end performs the master output.

33. The method of claim 32, wherein the operating assist portion is coupled to the first slave end and to the input device.

* * * * *